(12) United States Patent
Fontaine

(10) Patent No.: US 6,629,603 B1
(45) Date of Patent: Oct. 7, 2003

(54) PORTABLE GARGLING SOLUTION PACKET

(76) Inventor: Edwina K. Fontaine, 632 E. Washington St., Chambersburg, PA (US) 17201

( * ) Notice: Subject to any disclaimer, the term of this patent is extended or adjusted under 35 U.S.C. 154(b) by 10 days.

(21) Appl. No.: 09/998,994

(22) Filed: Nov. 24, 2001

Related U.S. Application Data

(63) Continuation-in-part of application No. 09/649,879, filed on Aug. 28, 2000, now abandoned.

(51) Int. Cl.[7] ............................. F24J 1/00; B65D 73/00
(52) U.S. Cl. ...................... 206/438; 206/828; 206/484; 126/263.02
(58) Field of Search ................ 206/438, 484, 206/822, 828; 126/263.02

(56) References Cited

U.S. PATENT DOCUMENTS

| | | | | |
|---|---|---|---|---|
| 3,891,138 A | * | 6/1975 | Glas | 206/484 |
| 4,106,478 A | * | 8/1978 | Higashijima | 126/263.02 |
| 4,276,263 A | * | 6/1981 | Andersen et al. | 206/484 |
| 4,756,299 A | * | 7/1988 | Podella | 126/263.02 |
| 5,117,809 A | * | 6/1992 | Scaringe et al. | 126/263.07 |
| 5,465,707 A | * | 11/1995 | Fulcher et al. | 126/263.07 |

FOREIGN PATENT DOCUMENTS

JP  02082910 A  *  3/1990  ............ A47J/36/30

* cited by examiner

*Primary Examiner*—Mickey Yu
*Assistant Examiner*—Gregory Pickett
(74) *Attorney, Agent, or Firm*—Goldstein & Lavas, P.L.

(57) ABSTRACT

A portable gargling solution packet including a package having an interior and an openable upper end. The interior is defined by opposed side walls. A saline solution is disposed within the interior of the package. A heat producing chemical lining is disposed within at least one of the opposed side walls of the package. When the openable upper end is opened the heat producing chemical lining reacts to outside air to cause an exothermic reaction to heat the saline solution.

2 Claims, 2 Drawing Sheets

PORTABLE GARGLING SOLUTION PACKET

CROSS REFERENCES AND RELATED SUBJECT MATTER

This application relates to subject matter contained in patent application Ser. No. 09/649,879, now abandoned, filed in the United States Patent Office on Aug. 28, 2000, and is a continuation-in-part of said application.

BACKGROUND OF THE INVENTION

The present invention relates to a portable gargling solution packet and more particularly pertains to a portable gargling solution packet which is self contained and which heats a salt water gargling solution just prior to use.

Gargling with salt water is an often prescribed treatment for a variety of oral ailments, and following oral surgery. Doctors and dentists alike will often instruct a patient to gargle with salt water several times a day for a prescribed time period.

Generally, warm water has greater therapeutic and soothing effects than cold water. Accordingly, it is typically recommended that the patient gargle with warm salt water. However, heated water is not always available. Considering the active lifestyle of. many individuals, it is then not always possible to gargle at the prescribed times.

The use of portable heating devices is known in the prior art. More specifically, portable heating devices heretofore devised and utilized for the purpose of heating water and the like are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,320,626 to Donnelly discloses a container comprised of a hollow body for storing liquids and includes a lid with thermoelectric means for heating or chilling the contents. U.S. Pat. No. 5,524,820 to Regan discloses a portable heater used to warm water.

While these devices fulfill their respective, particular objective and requirements, the aforementioned patents do not describe a portable gargling solution packet for allowing a pre-mixed salt water solution to be heated just before use without the use of electricity or other independent sources of heat.

In this respect, the portable gargling solution according to the present invention substantially departs from the conventional concepts and designs of the prior art, and in doing so provides an apparatus primarily developed for the purpose of allowing a gargling solution to be formed upon activation by a heat source.

Therefore, it can be appreciated that there exists a continuing need for a new and improved portable gargling solution packet which can be used for allowing a gargling solution to be formed upon activation by a heat source. In this regard, the present invention substantially fulfills this need.

SUMMARY OF THE INVENTION

In the view of the foregoing disadvantages inherent in the known types of portable heating devices now present in the prior art, the present invention provides an improved portable gargling solution packet. As such, the general purpose of the present invention, which will be described subsequently in greater detail, is to provide a new and improved portable gargling solution packet which has all the advantages of the prior art and none of the disadvantages.

To attain this, the present invention essentially comprises a package having an interior and an openable upper end. The interior is defined by opposed side walls. A pre-mixed salt water solution is disposed within the interior of the package. A heat producing chemical lining is disposed within at least one of the opposed side walls of the package. The heat producing chemical lining reacts to outside air when the openable upper end is opened to heat the saline solution.

There has thus been outlined, rather broadly, the more important features of the invention in order that the detailed description thereof that follows may be better understood, and in order that the present contribution to the art may be better appreciated. There are, of course, additional features. of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved portable gargling solution packet which has all the advantages of the prior art portable heating devices and none of the disadvantages.

It is another object of the present invention to provide a new and improved portable gargling solution packet which may be easily and efficiently manufactured and marketed.

It is a further object of the present invention to provide a new and improved portable gargling solution packet which is of durable and reliable construction.

An even further object of the present invention is to provide a new and improved portable gargling solution packet which is susceptible of a low cost of manufacture with regard to both materials and labor, and which accordingly is then susceptible of low prices of sale to the consuming public, thereby making such a portable gargling solution economically available to the buying. public.

Even still another object of the present invention is to provide a new and improved portable gargling solution packet for allowing a gargling solution to be heated upon activation.

Lastly, it is an object of the present invention to provide a new and improved portable gargling solution including a package having an interior and an openable upper end. The interior is defined by opposed side walls. A pre-mixed saline solution is disposed within the interior of the package. A heat producing chemical lining is disposed within at least one of the opposed side walls of the package. The heat producing chemical lining reacts to outside air when the openable upper end is opened to heat the saline solution so that it may be used for gargling.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various figures.

DESCRIPTION OF THE PREFERRED EMBODIMENT

Figure 2:
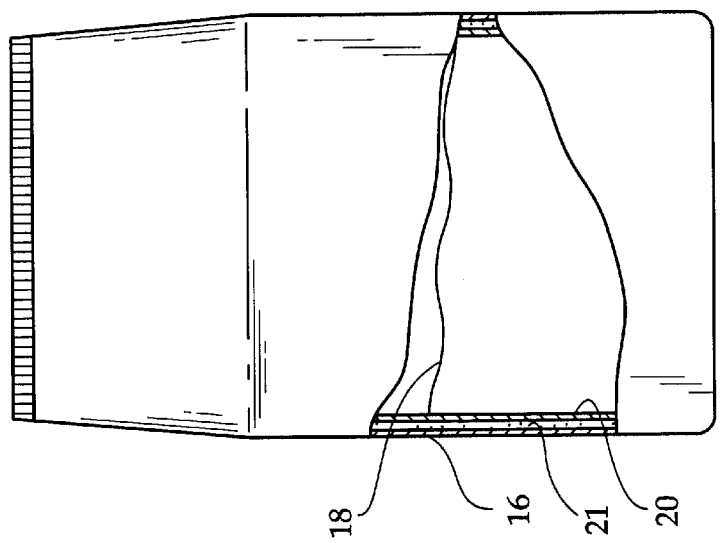
FIG. 2 is a front view of the present invention illustrating the saline solution disposed within the package prior to use.
Figure 1:
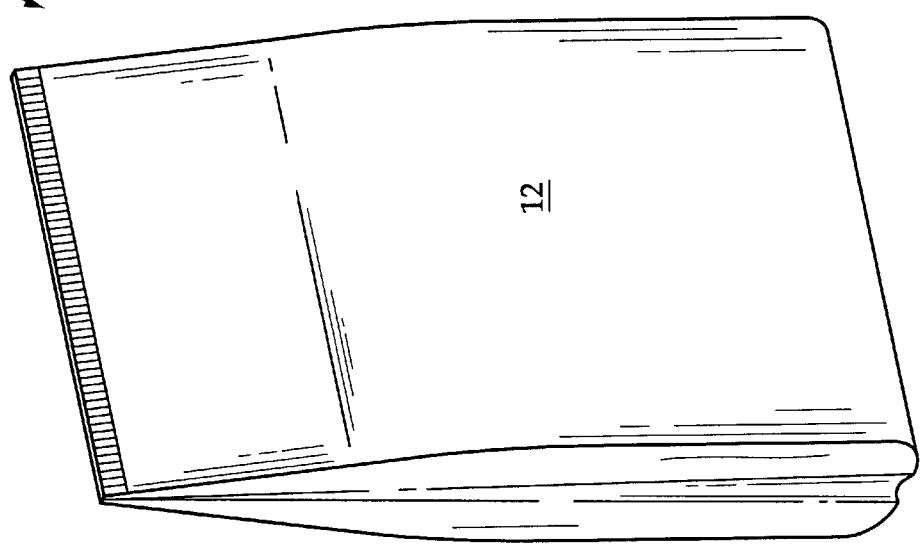
FIG. 1 is a perspective view of the preferred embodiment of the portable gargling solution packet constructed in accordance with the principles of the present invention.
Figure 3:
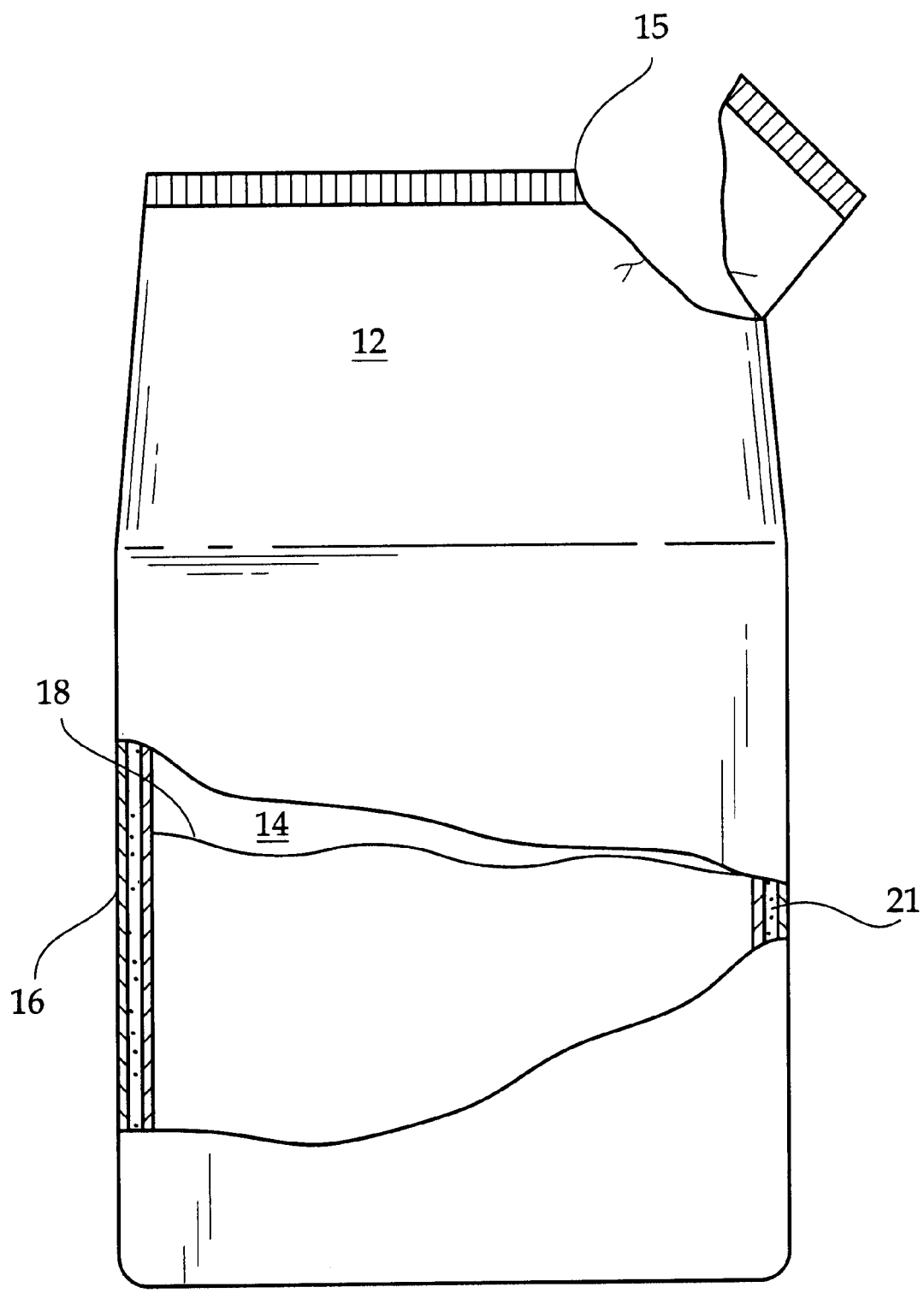
FIG. 3 is a front view of the present invention wherein the package has been opened to activate the heat source and heat the saline solution.

With reference now to the drawings, and in particular, to FIGS. 1 through 3 thereof, the preferred embodiment of the new and improved portable gargling solution packet embodying the principles and concepts of the present invention and generally designated by the reference number 10 will be described.

Specifically, it will be noted in the various figures that the device relates to a portable gargling solution for allowing a gargling solution to be formed upon activation by a heat source. In its broadest context, the device consists of a package, a pre-mixed saline solution, and a chemical heat producing source. Such components are individually configured and correlated with respect to each other so as to attain the desired objective.

The package 12 has an interior 14 and an openable upper end 15. The interior 14 is defined by opposed side walls 16. The package 12 would be constructed of similar materials known in the art that are used to hold medicinal items and the like.

A premixed saline solution 18 is disposed within the interior 14 of the package 12. The saline solution, 18 is a salt and water mixture, of a concentration suitable for gargling.

The heat producing chemical lining 20 is disposed within at least one of the opposed side walls 16 of package 12. The heat producing chemical lining 20 contains a ehat source 21 which is capable of producing heat through an exothermic reaction when activated by the user. Preferably, the exothermic reaction occurs upon exposure to air, so that when the openable upper end 15 is opened, the heat source 21 produces sufficient heat to warm the saline solution 18. Although the heat source 21 is isolated from the saline solution 18, both the interior 14 and the cavity containing the heat source 21 are opened when the openable upper end 15 is "ripped", as seen in FIG. 3. Suitable heat sources are known in the prior art. For example, U.S. Pat. No. 4,106,478 to Higashijima discloses a packaged heat generator which produces heat upon contact with air. Other suitable heat source may include multi-chambered structures where two chemical components are isolated, and then produce heat when suddenly mixed. In the context of the present invention, the chemical lining 20 could be such a multi-chambered structure where two chemical containing compartments are separated by a thin membrane, which is broken just prior to use, and imparts heat into the interior 14, which is impermeable to contamination from the chemicals. However, if a chemical heat source were devised or is available which is safe for consumption, yet was activatable upon contact with water, the package could be made so that just prior to use the water in the interior 14 suddenly mixes with the heat source 21.

In use, the present invention would only operate when the heat source is activated, which may be by opening the package 12 to expose the heat producing lining 20 to air. When the package 12 is opened, the heat source 20 will react with the air to heat the saline solution 18. This liquid solution 18 that is heated may be drank directly from the package 12, or can be poured into a glass. The user can gargle the solution 18 to treat sore gums and throats to realize the medicinal benefits normally associated with a saline solution.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is notdesired to limit the invention to the exact construction and operation shown and described, and accordingly, all suitable modifications and equivalents may be resorted to, falling within the scope of the invention.

What is claimed is:

1. A portable gargling solution packet for allowing a gargling solution to be formed upon activation by a heat source comprising, in combination:

a package having an interior and an openable upper end, the interior being defined by two opposed pairs of side walls;

a solution comprising essentially salt and water; and a heat producing chemical lining disposed between the side walls of at least one of the pairs of the opposed side walls of the package, the heat producing chemical activatable to heat the solution, said heat producing chemical lining further comprising a heat source which is isolated from the interior, but is exposed to air when the openable upper end is opened, the heat source produces an exothermic reaction when exposed to air.

2. A portable gargling solution method, using a package having an interior and an openable upper end, the interior being defined by opposed side walls containing a saline solution within the interior, the package having a chemical heat source, comprising the steps of:

opening the upper end;

warming the saline solution within the packet by activating the chemical heat source by opening the upper end and exposing the chemical heat source to air;

pouring the warmed saline solution from the packet; and gargling with the saline solution.

* * * * *